(12) United States Patent
Van Kesteren

(10) Patent No.: US 7,814,777 B2
(45) Date of Patent: Oct. 19, 2010

(54) BACKGROUND ACOUSTIC SIGNAL SUPPRESSION IN PHOTOACOUSTIC DETECTOR

(75) Inventor: Hans Van Kesteren, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 760 days.

(21) Appl. No.: 11/722,358

(22) PCT Filed: Dec. 29, 2005

(86) PCT No.: PCT/IB2005/054423

§ 371 (c)(1),
(2), (4) Date: Jun. 21, 2007

(87) PCT Pub. No.: WO2006/072867

PCT Pub. Date: Jul. 13, 2006

(65) Prior Publication Data

US 2010/0020326 A1    Jan. 28, 2010

(30) Foreign Application Priority Data

Jan. 3, 2005    (EP) ................................. 05300002

(51) Int. Cl.
*G01N 29/02*    (2006.01)

(52) U.S. Cl. ..................................... 73/24.01

(58) Field of Classification Search .................. 73/24.01
See application file for complete search history.

(56) References Cited

U.S. PATENT DOCUMENTS

| | | | | |
|---|---|---|---|---|
| 4,412,445 A | * | 11/1983 | Spellicy | 73/24.02 |
| 5,780,724 A | * | 7/1998 | Olender et al. | 73/24.01 |
| 6,834,548 B1 | * | 12/2004 | Hibbs | 73/579 |
| 2005/0279170 A1 | * | 12/2005 | Okumura et al. | 73/602 |

* cited by examiner

*Primary Examiner*—Hezron Williams
*Assistant Examiner*—Alex Devito

(57) ABSTRACT

The present invention relates to a photo-acoustic device (100) for photo-acoustic analysis of a sample such as exhaled human breath. The device includes a sample cell cavity (102) for containing the sample (116), a first light source (130) outside the sample cell cavity for emitting a first modulated light beam (114) at a wavelength in an absorbing range of the searched component. The first light beam is led into the cavity through a transparent cavity wall (106). The searched gas component absorbs the first light beam and first acoustic waves are thus generated which are picked up by the microphone (110). The microphone also picks up background acoustic waves caused by the laser light beam going trough the cavity wall. The device is further equipped with a noise cancellation system (120, 122) that generates a second set of acoustic waves in anti-phase with the background acoustic waves.

10 Claims, 1 Drawing Sheet

BACKGROUND ACOUSTIC SIGNAL SUPPRESSION IN PHOTOACOUSTIC DETECTOR

The present invention relates to the detection of components in solution samples by photo-acoustic sensors. The invention is particularly relevant to gas sensing in industrial processes, environmental gas sensing and in the medical field for the non-intrusive analysis of gaseous, solid or liquid substances rejected by the human body. One major application is the non-intrusive analysis of exhaled breath.

Breath testing is developing rapidly into an exciting area of medical technology. Testing for components in exhaled breath is a non-invasive, patient friendly and low cost medical procedure. Prime examples of breath testing are monitoring of asthma, detection of alcohol in the breath, stomach disorders or the detection of acute organ rejection and first clinical trials show possible applications in the pre-screening of breast and lung cancers.

Various solutions are available to detect diagnosis components in exhaled breath. Diagnosis components are abnormal components or abnormal concentrations of components normally present in the human exhaled breath that may indicate a disease, a disorder or an abnormal state of the patient. These components may be factors that would lead to a diagnosis but they may not on their own. These diagnosis components, also called biomarkers, have typical concentrations in the parts per million to parts per trillion range. Nitric oxide is a well-known biomarker and elevated concentrations of nitric oxide can be found in asthmatic patients. Currently, exhaled nitric oxide levels at the parts per billion concentrations can only be measured using expensive and bulky equipment based on chemiluminescence.

The invention is in the field of photo-acoustic sensors. Such sensors operate on the basis of the photo-acoustic principle, whereby modulated-light illumination of a sample containing components to be detected gives rise to an acoustic wave. An acoustic sensor, e.g. a microphone, captures the sound waves and generates a signal therefrom at its output, which is directly correlated to the concentration of the component in the gas sample. The acoustic wave arises as one or more of the sample components absorb the light radiation and consequently the sample heats up and expands. As the material expands and contracts upon modulated light exposure, sound waves are generated. The absorbing component concentration can be inferred from the magnitude of the sound waves. Different sample components are distinguished by use of light sources having different wavelengths corresponding to the specific absorption wavelengths of the components. In a typical photoacoustic gas sensor, a resonant acoustic cavity or sample cell is used to amplify sound waves, thereby increasing detection sensitivity.

Background signals may limit the minimum concentration detection level of sample components. Background signals may have different origins and interference signals may be caused in gas samples, by for instance, air-flow and variations in the air pressures as a result, wall effects, vibrations and even irradiation of the microphone membrane in sensors where the light beam reaches the microphone. A portion of the background signal is also caused by the expansion of the gas cavity itself created by the irradiation by the light beam. Partial solutions have been proposed to remedy at least one of the background signal sources and the industry is still in need for solutions that would reduce the impact of background signals caused by the cavity walls absorbing a portion of the entering light beam.

One solution is proposed in U.S. Pat. No. 6,006,585 for an optoacoustic gas sensor. The sensor has a sensor body, a light source, a measurement cell with a gas-permeable membrane, a measurement microphone, and an optical measurement filter between the light source and the measurement cell. The sensor also includes a reference cell separate from the measurement cell. The reference cell has a reference microphone that is shielded against optoacoustic signals from the gas to be detected via the reference cell being substantially free from intensity-modulated optical radiation having an absorption wavelength of the gas to be detected. The measurement signal, which indicates gas concentration, is obtained by subtraction of the signals from the two microphones. As a result of the subtraction, interference signals caused by the vibrations or air pressure fluctuation are eliminated, the former through the user of the reference microphone which receives no optoacoustic signals from the gas to be measured, and the latter by virtue of the spatially separate reference cell with the reference microphone.

Half of the gas cell volume is devoted to background-signal suppression and existing solutions like the above that remedy interference noise signals are often bulky and expensive. These drawbacks limit the miniaturization of such device categories and their market acceptance. Indeed miniaturized trace-gas sensors are essential for personal health care applications.

It is an object of one or more embodiments of the invention to devise a versatile reasonably sized exhaled breath apparatus. It is another object of the invention to provide an apparatus that offers high sensitivity while not compromising on the size of the overall device.

To this end, an apparatus of the invention first includes a sample cell cavity containing the sample and a first light source outside the gas cell cavity emitting a first modulated light beam at a wavelength in an absorbing range of the potential component. The gas cell includes a cavity wall that guides into the cavity the first light beam. A microphone captures sound vibrations generated by the potential gas component when absorbing the first light beam. The apparatus is further equipped with an anti-sound generating system generating sound signals in anti-phase with sound signals caused by the absorption of the first light beam by the transparent wall.

The invention is based on the premises that background signal reduces the system's sensitivity and that very low concentrations of biomarkers may not be detected from the patient's exhaled breath though they would be a clinical indication of an abnormal physical condition, such as organ rejection, stress, or the like. The inventors have realized that one great source of background noise is the absorption of the laser beam by the cavity wall and more particularly the transparent plate through which the laser beam is guided into the cavity. Absorption of the laser beam by the entrance wall causes the generation of a second acoustic wave that competes with the first acoustic wave generated by the absorption of biomarkers present in the exhaled breath. The invention proposes to counter the second acoustic wave by generating an acoustic wave signal that is in anti-phase with the background second acoustic wave and consequently annuls it. A background cancellation arrangement of small size may be devised by one-skilled-in-the-art to generate the anti-phase acoustic wave. An advantage of the invention is to increase the sensitivity of an opto-acoustic sensor without increasing its size.

In an embodiment of the invention, the anti-sound generating system includes a second light beam source that generates a second light beam at a wavelength outside the absorption range of the searched component and that is further in anti-phase with the first light beam. In this embodiment, the second laser beam will be absorbed by the transparent cavity wall and because the second laser beam is in anti-phase with the first laser beam, the acoustic wave generated by the cavity wall absorbing the second laser beam will also be in anti-phase with the acoustic wave caused by the absorption by the cavity wall of the first light beam. The two acoustic waves will compensate and the noisy interference is annulled.

In another embodiment, the anti-sound generating system includes a transparent electrically conducting coating affixed to the cavity wall. Passing a current in the coating will cause the generation of an acoustic wave whose phase and intensity may be determined to compensate for the noisy acoustic wave generated by the transparent cavity wall.

The invention also pertains to a method for detecting the presence of a potential component in a gas sample.

These and other aspects of the invention will be apparent from and will be elucidated with reference to the embodiments described hereinafter.

The present invention will now be described in more detail, by way of example, with reference to the accompanying drawings, wherein.

Throughout the drawing, the same reference numeral refers to the same element, or an element that performs substantially the same function.

Figure 1:
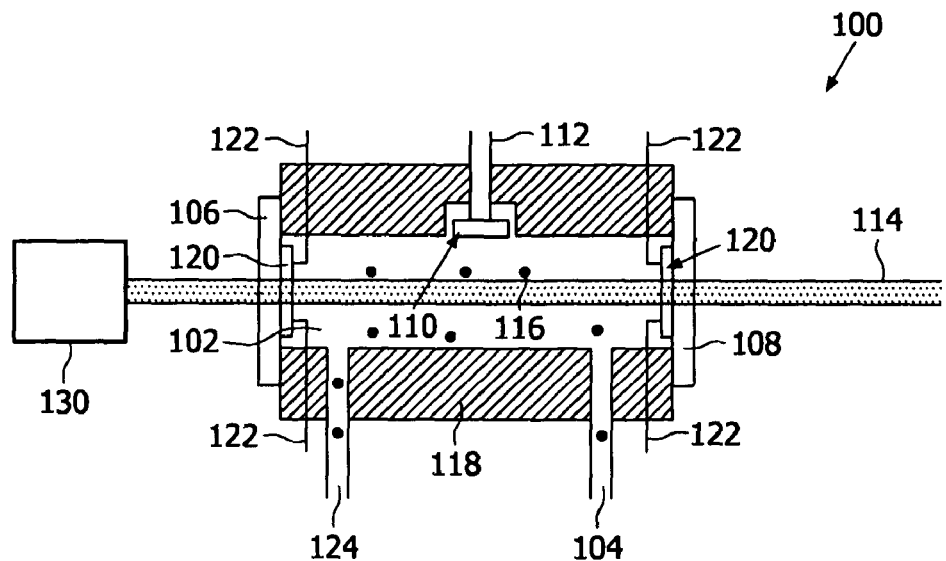
FIG. 1 is a first exemplary embodiment of an apparatus of the invention.

FIG. 1 shows one exemplary embodiment of a photoacoustic sensor 100 of the invention. Sensor 100 includes a cavity 102, which contains gas sample 116. Gas sample 116 is lead into cavity 102 via gas-in tube 124 and sample 116 leaves cavity 102 via gas-out tube 104. In the embodiment, gas sample 116 contains at least one component whose presence and/or composition will be partly analyzed by sensor 100 through light absorption by the component. In this embodiment, the chosen component is such that an unusually high, i.e. above normal, concentration of the searched component would be an indication of a medical condition, e.g. physical distress, sickness, organ rejection, respiratory crisis and the like. An apparatus of the invention is a non-invasive tool that helps practitioners establish a diagnosis by providing accurate patients' physical data to them. Detection of an abnormal concentration of one component, which will be measured in the parts per billion, or detection of a component not present in normal condition is performed as follows.

Sensor 100 may have a tubular shape with two openings 124, 104 bored in its opaque cylindrical lateral wall 118 that let gas in and out from cavity 102. The dimensions of the sensor 100 are chosen in such a way that cavity 102 exhibits an acoustic resonance at the amplitude-modulation frequency of the light from source 130. Transparent plates 106 and 108 are placed at each respective end and hermetically seals cavity 102 containing gas sample 116. Transparent plates 106 and 108 may be made out of glass, CaF2, ZnSe or polymers or any other light-transmitting material. A material is however chosen that shows minimal absorption at the wavelength of the light used for sensing the searched gas component. Transparent plate 106 leads a laser light beam 114 from laser source 130 into cavity 102 and laser light beam 114 exits cavity 102 through transparent plate 108. Detection of the searched component is based on the principle that laser light beam 114 will be absorbed by the searched component particles and in result to the absorption, the particles will be excited and expand and a sound wave will result. The sound wave is picked up by microphone 110 placed in recess in cavity's 102 internal wall. Microphone 110 produces a signal on leads 112 representative of the magnitude of the acoustic wave picked up by microphone's 110 membrane. Microphone 110 is shielded in cavity 102 from laser light beam 114 to prevent any interaction of laser beam 114 and the microphone's membrane which would generate a background signal and influence the overall device's sensitivity.

Laser source 130 generates a laser light beam at a wavelength within the absorption range of the searched component. Nitric Oxide is a well-known gas component present in the human breath, and elevated concentrations of NO can be found in asthmatic patients. NO shows a number of absorption lines around a wavelength of 5 μm. One of these absorption lines can be exploited for photo acoustic detection of the NO concentration by for instance a quantum cascade semiconductor laser with a device structure optimized for emission at this appropriate wavelength. Although many trace-gases show absorption lines in the mid-infrared, the described embodiment can as well be used in the visible and UV range with the appropriate choice of light source and plate material.

Even with plate materials with minimal absorption as the laser wavelength, a small amount of laser light beam 114 will still be absorbed by transparent plate 106 when laser light beam 114 enters cavity 102 and goes trough plate 106 and a small amount of laser light beam 114 may also be absorbed by transparent plate 108 when laser light beam 114 exits cavity and traverses plate 108. This absorption of the laser beam will lead to small yet noticeable heating of the air film at the surface of plates 106 and 108 and the generation of an acoustic pressure wave that will also be picked up by microphone 110. This generated background signal limits the minimum detectable trace gas concentration and thus limits sensor's 100 sensitivity.

A solution to compensate for the background acoustic wave is proposed hereinafter. The sensor 100 of FIG. 1 is further equipped with an anti-sound generation system. The exemplary anti-sound generation system includes transparent electrically conductive coatings 120 affixed to both plates 106 and 108. Electrical wires 122 connect to respective coatings 120 and upon activation cause a current to flow through coatings 120. The amplitude-modulated current flowing through coatings 120 heats up by Joule's effect the air in the vicinity of the surface of plates 106 and 108 and an acoustic wave results. By periodic heating of coatings 120 with a well chosen amplitude and modulation one can generate an acoustic wave in anti-phase with the background acoustic wave generated by plates 106 and 108 absorbing laser light beam 114 and canceling this background signal wave. Examples of transparent electrically conductive coatings include Indium Tin Oxide (ITO), hydrogenated amorphous Silicon and hydrogenated amorphous Germanium. The choice will again depend on the wavelength of the applied light and minimal thin-film absorption at this wavelength. Prior experiments are carried out to determine the amplitude and periodicity of the heating required to cancel out the background acoustic wave generated by plates 106 and 108. To this end, cavity 102 is filled-in with a gas that will not absorb the first laser light beam 114 so that the only acoustic wave due to the first laser beam 114 will be that caused by the heating of transparent plates 106 and 108. The amplitude and periodicity of the electrical current passed trough coatings 120 will be obtained by minimizing the total acoustic wave picked up by microphone 110.

Figure 2:
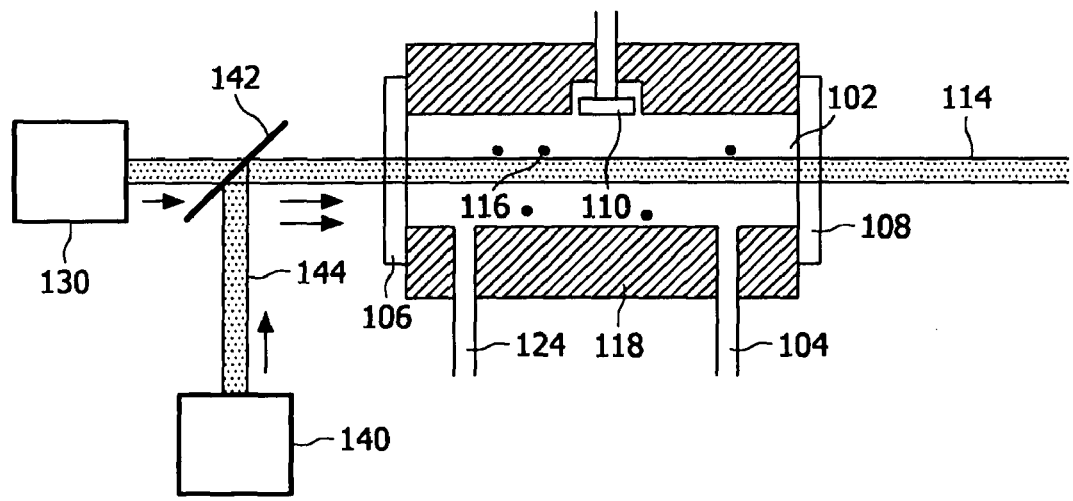
FIG. 2 is a second exemplary embodiment of an apparatus of the invention.

FIG. 2 shows another exemplary embodiment of a sensor device 100 of the invention. Sensor 100 of FIG. 2 is similar to sensor 100 of FIG. 1 and includes cavity 102, gas-in tube 124, gas-out tube 104, transparent plates 106, 108, microphone 100 and wall 118. In this embodiment, the background signal cancellation arrangement includes dichroic mirror 142 and laser beam source 140 that generates a second laser light beam guided into cavity 102. Laser beam 140 produces a second laser light beam 144 with a wavelength outside the absorption range of the searched component or any other component of gas sample 116 so that no additional background acoustic wave is generated by second laser light beam 144 passing through cavity 102.

In a similar fashion to the prior experiments carried out in the context of the embodiment of FIG. 1, prior experiments are carried out as well to determine the intensity of laser light beam 144 needed to cancel out the background acoustic wave. Sensor 100 is turned on with cavity 102 filled in with gas that does not react to laser beams 114 and 144. The intensity of laser beam source 140 is adjusted so that the acoustic wave generated at the plate by laser beam 144 and the acoustic waves caused by laser beam 114 traversing plates 106 and 108 cancel out each other. Laser beam 144 is in anti-phase with laser light beam 114. Both background acoustic waves cancel out each other so that no signal is picked up by microphone 110. A complete background signal cancellation may not be practically feasible but minimization of the total background signal will lead to the laser beam source 140 intensity value that optimizes sensor's 100 sensitivity.

The foregoing merely illustrates the principles of the invention. It will thus be appreciated that those skilled in the art will be able to devise various arrangements which, although not explicitly described or shown herein, embody the principles of the invention and are thus within the spirit and scope of the following claims.

The structural representation of sensor 100 in FIG. 1 is only given as an exemplary illustration of the invention and should not be constrained to limit the scope of the invention. For example, the alignment of laser source 130, transparent plates 106 and 108 is only a proposed implementation and an arrangement of mirrors and/or partially refractive materials may be devised by one-skilled-in-the-art to let laser light beam enter cavity 102. In a similar fashion, the shape and the internal structure of sensor 100 is only given here as an example and should not be used to restrict the scope of the invention.

In interpreting these claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) each of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise; and h) no specific sequence of acts is intended to be required unless specifically indicated.

The invention claimed is:

1. A photo-acoustic device (100) for detecting the presence of a searched component in a sample (116), the device comprising:
   a sample cell cavity (102) containing the sample;
   a first light source (130) outside the sample cell cavity (102) emitting a first modulated light beam (114) at a wavelength in an absorbing range of the searched component;
   a cavity wall (106) for guiding the first light beam into the cavity;
   an acoustic pickup unit (110) for capturing first acoustic waves generated in part by the searched component absorbing the first light beam;
   characterized in that,
   the device is further equipped with a background acoustic wave cancellation system (120, 122, 140, 144) that generates a second set of acoustic waves in anti-phase with background acoustic waves caused by the absorption of the first light beam by the cavity wall and the second set of acoustic waves cancel out the background acoustic waves at the acoustic pickup unit.

2. The device of claim 1, characterized in that the cavity wall generates the background acoustic waves by the first light beam crossing and heating the cavity wall.

3. The device of claim 1, characterized in that the acoustic pick up unit includes a microphone.

4. The device of claim 1, characterized in that the background acoustic wave cancellation system includes a second light beam source (140) for generating a second light beam (144) at a wavelength outside the absorption range of the searched component.

5. The device of claim 4, characterized in that the background acoustic wave cancellation system is further configured to generate the second set of acoustic waves with an intensity obtained from a minimization of total acoustic waves picked up by the acoustic pickup unit and caused by absorption of the cavity wall of the two light beams in the sample cavity filled with.

6. The device of claim 4, further comprising:
   a dichroic mirror (142) for guiding the second laser light beam into the cavity.

7. The device of claim 1, characterized in that the background acoustic wave cancellation system includes a transparent electrically conducting coating affixed to the cavity wall.

8. The device of claim 1, characterized in that the electrically conductive coating is passed with a current with an intensity obtained from a minimization of total acoustic waves picked up by the acoustic pickup unit caused by the absorption of the cavity wall of the first light beam and caused by heating of the cavity wall due to the current passing through the electrically conductive coating in the sample cavity filled in with a sample that does not absorb the first light beam.

9. The device of claim 1, characterized in that the sample cell cavity is configured to contain a liquid sample or a gaseous sample.

10. A method for detecting the presence of a searched component in a sample (116), the method comprising:
- containing the sample in a sample cell cavity (102);
- emitting a first modulated light beam at a wavelength in an absorbing range of the searched component;
- guiding the first light beam (114) into the cavity by means of a cavity wall;
- capturing using an acoustic pick-up unit (110) a first set of acoustic waves caused at least by the searched component absorbing the first light beam;

characterized in that the method further comprises:
- emitting a second set of acoustic waves in anti-phase with background acoustic waves caused by the absorption of the first light beam by the cavity wall.

* * * * *